United States Patent
Bafus et al.

(10) Patent No.: US 6,576,647 B2
(45) Date of Patent: Jun. 10, 2003

(54) PSEUDOPOLYMORPH OF (—)-CIS-2-(2-CHLOROPHENYL)-5,7-DIHYDROXY-8[4R-(3S-HYDROXY -1-METHYL)PIPERIDINYL]-4H-1-BENZOPYRAN-4-ONE

(75) Inventors: Gary L. Bafus, Blue Spring, MO (US); Christine M. Harrison-Bowman, Overland Park, KS (US); Gary Lee Silvey, Overland Park, KS (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/760,589

(22) Filed: Jan. 16, 2001

(65) Prior Publication Data

US 2003/0045551 A1 Mar. 6, 2003

Related U.S. Application Data

(60) Provisional application No. 60/266,307, filed on Jan. 18, 2000.

(51) Int. Cl.[7] .............................................. A61K 31/445
(52) U.S. Cl. ........................................ 514/320; 546/197
(58) Field of Search ........................... 514/320; 546/197

(56) References Cited

U.S. PATENT DOCUMENTS

| | | | |
|---|---|---|---|
| 4,900,727 A | 2/1990 | Kattige et al. | 514/320 |
| 5,284,856 A | 2/1994 | Naik et al. | 514/212 |
| 5,908,934 A * | 6/1999 | Kim | 546/216 |

FOREIGN PATENT DOCUMENTS

| | | |
|---|---|---|
| EP | 0366061 | 2/1990 |

OTHER PUBLICATIONS

Cheronis "Semimicro experimental organic chemistry" deGratt, p.67–69 (1958).*

Fox et al. "Physic and chemistry of the organic solid state" Inter Sci. p. 179–182 (1963).*

Li, Ping et al: "Evaluation of Intravenous Flavopiridol Formulations" PDA J. Phar. Sci. Technol. (1999), 53(3), 137–140.

Sedlacek et al.: "Flavopiridol, a New Kinase Inhibitor for Tumor Therapy", Int. J. Oncology, vol. 9, pp. 1143–1168.

* cited by examiner

Primary Examiner—Ceila Chang
(74) Attorney, Agent, or Firm—Lawrence Martin; Balaram Gupta

(57) ABSTRACT

The present invention comprises a pseudopolymorph of (–)-cis-2-(2-chlorophenyl)-5,7-dihydroxy-8[4R-(3S-hydroxy-1-methyl)piperidinyl]-4H-1-benzopyran-4-one hydrochloride, a method of making same, a pharmaceutical composition and methods of using the pseudopolymorph.

22 Claims, 1 Drawing Sheet

Estimated Detection Limit

HMR 1275 Form II in Form I Bulk Drug Substance

PSEUDOPOLYMORPH OF (—)-CIS-2-(2-CHLOROPHENYL)-5,7-DIHYDROXY-8[4R-(3S-HYDROXY -1-METHYL)PIPERIDINYL]-4H-1-BENZOPYRAN-4-ONE This application claims the benefit of U.S. Provisional application No. 60/266,307, filed Jan. 18, 2000.

BACKGROUND OF THE INVENTION

The compound (-)-cis-2-(2-chlorophenyl)-5,7-dihydroxy-8[4R-(3S-hydroxy-1-methyl)piperidinyl]-4H-1-benzopyran-4-one or one of its pharmaceutically acceptable salt forms (known as "Flavopiridol") is an immunomodulator and antiinflammatory agent (U.S. Pat. No. 4,900,727), and inhibitor of oncogene-encoded kinases or growth factor receptor tyrosine kinases (U.S. Pat. No. 5,284,856). Flavopiridol is a strong inhibitor of cyclin dependent kinases (CDKs) including CDK1, CDK2, CDK4, CDK6 and CDK7, (cdk1/clyclin B; cdk2/cyclin A; cdk2/cyclin E; cdk4/cyclin D; cdk6/cyclinD; cdk7/cyclin H) with the potential to cause inhibition of cell cycle progression in $G_1$ and $G_2$ by multiple mechanisms relatable to cdk inhibition. See *International Journal of Oncology* 9:1143–1168 (1996). Also, Flavopiridol has been shown to inhibit the EGF receptor family, the receptor associated SRC family kinases, and signal transducing kinases. In vitro and in vivo experiments have shown that Flavopiridol is able to inhibit a broad type range of human tumors, leukemias and lymphomas.

(-)-cis-2-(2-chlorophenyl)-5,7-dihydroxy-8[4R-(3S-hydroxy-1-methyl)piperidinyl]-4H-1-benzopyran-4-one or a pharmaceutically acceptable salt thereof crystallizes into numerous solvates with solvents such as ethanol, DMSO, methanol, acetonitrile/isopropanol, ethanol/isopropanol, and isopropanol and solvate hydrates such as ethanol/ and isopropanol/water combinations. The preferred form is the Flavopiridol hydrochloride ethanol/water solvate form (hereafter "Form II").

Although Form II meets pharmaceutical standards, it has a tendency to absorb water if not packaged in water impermeable packaging, which increases cost of production. It is also desirable to have as much stability as possible in the crystalline structure for handling purposes and for approvals through different pharmaceutical regulatory agencies throughout the world.

It is an object of the present invention to provide a form of Flavopiridol as Form I which has superior physical characteristics for use as a pharmaceutical composition.

SUMMARY OF THE INVENTION

The present invention comprises pseudopolymorph Form I as defined by x-ray powder diffraction. Preferably, Form I is essentially free of Form II and/or other Flavopiridol forms. It is useful in a pharmaceutical composition comprising an effective amount of Form I and a pharmaceutically acceptable carrier. Form I is useful as a protein kinase inhibitor, cyclin dependent kinase inhibitor, and in the treatment for various forms of cancer.

Form I is further characterized by its ability of being less hygroscopic than Form II e.g., has less weight gain in comparative relative humidities.

Form I is prepared by combining a sufficient quantity of Form II with a sufficient amount of an appropriate azeotropic solvent thus forming an azeotropic mixture; submitting the azeotropic mixture to azeotropic distillation sufficient to form Form I; and optionally recovering Form I therefrom.

Figure 1:
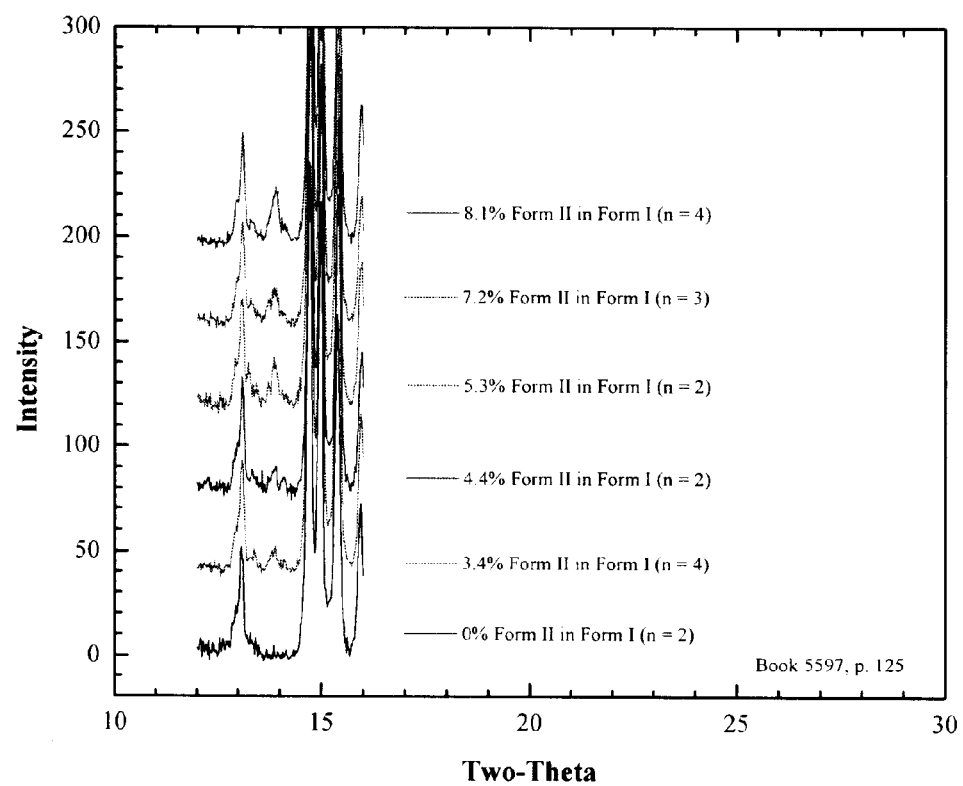
FIG. 1: Estimated Limit of Detection of Form II in Form I by X-ray Powder Diffraction (XRPD)

To estimate the limit of detection of Form II in Form I, varying quantities of Form II were accurately weighed and carefully mixed (unmilled) with Form I. The entire mixture was transferred to a platinum sample holder and leveled using glass microscope slide. All samples were scanned at 0.2°/min. from 12°–16° 2⊖. At a minimum, duplicate determinations were made at each spike level, the XRPD patterns averaged, and the peak height at ~13.8° 2⊖ measured to the nearest 0.1 mm. The estimated detection limit of Form II in Form I is ~3%.

DETAILED DESCRIPTION OF THE INVENTION

"Form I" means (-)-cis-2-(2-chlorophenyl)-5,7-dihydroxy-8[4R-(3S-hydroxy-1-methyl)piperidinyl]-4H-1-benzopyran-4-one hydrochloride. It has the same active ingredient as Flavopiridol but differs from known crystals of Flavopiridol in that it is anhydrous and/or solvate free, i.e., a pseudopolymorph of known forms of Flavopiridol.

Form I is identified by x-ray diffraction patterns expressed in terms of "d" spacing using Cu K-alpha radiation as follows:

D space-Å
12.708
4.323
5.594
5.349
3.590,
and more preferably as:
D space-Å
12.708
4.323
5.594
5.349
3.590
3.366
4.209
3.395
3.438
4.839.

Also, Form I is identified by x-ray diffraction patterns expressed in terms of "d" spacing using Cu K-alpha radiation and the Relative Intensities thereof:

| D space - Å | Relative Intensities |
|---|---|
| 12.708 | Strong |
| 4.323 | Strong |
| 5.594 | Strong |
| 5.349 | Medium |
| 3.590 | Medium |
| 3.366 | Medium |
| 4.209 | Medium |
| 3.395 | Medium |
| 3.438 | Medium |
| 4.839 | Medium. |

More preferably, Form I is identified by X-ray diffraction patterns expressed in terms of "d"spacing using Cu K-alpha radiation and the Relative Intensities (RI) percentages thereof:

| D space - Å | Relative Intensity % |
| --- | --- |
| 12.708 | 100.0 |
| 4.323 | 75.9 |
| 5.594 | 58.5 |
| 5.349 | 49.5 |
| 3.590 | 46.6 |
| 3.366 | 42.0 |
| 4.209 | 40.7 |
| 3.395 | 39.5 |
| 3.438 | 38.8 |
| 4.839 | 37.1. |

Form I X-ray powder diffraction is more fully described in Table 1.

TABLE 1

| 2 Theta Angle (°) | D Space - Å | Relative Intensity | Relative Intensity (%) |
| --- | --- | --- | --- |
| 6.950 | 12.708 | Strong | 100.0 |
| 20.529 | 4.323 | Strong | 75.9 |
| 15.830 | 5.594 | Strong | 58.5 |
| 16.560 | 5.349 | Medium | 49.5 |
| 24.778 | 3.590 | Medium | 46.6 |
| 26.457 | 3.366 | Medium | 42.0 |
| 21.091 | 4.209 | Medium | 40.7 |
| 26.226 | 3.395 | Medium | 39.5 |
| 25.898 | 3.438 | Medium | 38.8 |
| 18.320 | 4.839 | Medium | 37.1 |
| 8.308 | 10.634 | Medium | 35.7 |
| 23.748 | 3.744 | Medium | 33.4 |
| 13.010 | 6.799 | Medium | 32.4 |
| 30.520 | 2.927 | Medium | 31.0 |
| 27.106 | 3.287 | Weak | 26.2 |
| 31.153 | 2.869 | Weak | 22.4 |
| 29.043 | 3.072 | Weak | 23.7 |
| 14.600 | 6.062 | Weak | 22.4 |
| 19.033 | 4.659 | Weak | 20.6 |

Form I is preferably essentially free of Form II and/or other forms of Flavopiridol. "Essentially free" of Form II and/or other forms of Flavopiridol means that Form II and/or other forms of Flavopiridol are present in less than 10%, 9%, 8%, 7%, 6%, 5%, 4% and 3% as shown by x-ray powder diffraction or Nuclear Magnetic Resonance (NMR).

"Other forms of Flavopiridol" include base and salt forms as is appropriate, and which include hydrates, solvates or solvate hydrates, but does not include Form I or Form II.

"Form II" means the solvate/hydrate of ethanol/water of (−)-cis-2-(2-chlorophenyl)-5,7-dihydroxy-8[4R-(3S-hydroxy-1-methyl)piperidinyl]-4H-1-benzopyran-4-one hydrochloride as described by x-ray powder diffraction in Table 2, obtained using Cu K-alpha radiation.

TABLE 2

| 2 Theta Angle (°) | D Space - Å | Relative Intensity (%) |
| --- | --- | --- |
| 6.920 | 12.763 | 100.0 |
| 13.850 | 6.389 | 35.7 |
| 27.908 | 3.194 | 22.2 |
| 6.669 | 13.244 | 18.0 |
| 20.838 | 4.259 | 13.8 |
| 7.339 | 12.036 | 13.8 |
| 31.660 | 2.824 | 9.5 |
| 10.208 | 8.659 | 8.3 |
| 14.722 | 6.012 | 7.2 |
| 16.413 | 5.397 | 6.9 |
| 25.829 | 3.447 | 6.5 |

Preferably, Form I is made by combining a sufficient quantity of Form II with a sufficient amount of an appropriate azeotropic solvent to form an azeotropic mixture; submitting the azeotropic mixture to azeotropic distillation sufficient to form Form I; and optionally recovering Form I.

A "sufficient quantity of Form II" is an amount to form crystals of Form I in the reaction mixture which can be recovered. One skilled in the art may experimentally determine this quantity.

A "sufficient quantity of a suitable solvent" is enough suitable solvent to at least partially dissolve Form II thus forming a reaction mixture and can be experimentally determined by one skilled in the art. The experiments described hereafter give examples of quantities that could be used.

"Appropriate conditions" in large part depend upon the suitable solvent selected. For example, if the appropriate conditions comprise azeoptropic distillation, an appropriate azeoptropic solvent will be selected.

A "suitable solvent" is a solvent that at least partially dissolves Form II, and permits the formation of crystals of Form I. The suitable solvent can be an "appropriate azeotropic solvent" or as otherwise described herein.

"Azeotropic mixture" refers to a liquid mixture of two or more substances which behaves like a single substance in that the vapor produced by partial evaporation of liquid has the same composition as the liquid. The constant boiling mixture exhibits either a maximum or minimum boiling point as compared with that of other mixtures of the same substance.

"Azeotropic distillation" refers to a type of distillation in which a substance is added to the mixture to be separated in order to form an azeotropic mixture with one or more of the constituents of the original mixture. Typically, the azeotropic mixture is heated to a temperature at which the solvate/water is driven off of Form II. The azeotropes thus formed will have boiling points different from the boiling points of the original mixture.

"Appropriate azeotropic solvent"(s), comprise ketone solvents such as acetone, methyl ethyl ketone and the like; aliphatic ester solvents such as ethyl acetate, methyl acetate, methyl formate, ethyl formate, isopropyl acetate and the like; mixtures of ketone solvents and aliphatic ester solvents; $C_5$–$C_8$ aliphatic solvents such as pentane, hexane and the like; aliphatic nitriles, such as acetonitrile; benzene, toluene, pyridine, and so on. See for example Practical Organic Chemistry, 3rd ed., John Wiley & Sons, 1956 e.g., pp. 10–11, incorporated herein by reference.

As used herein, the term "suitable temperature" refers to that temperature which permits the crystallization of Form I without substantial damage to the Form I thus formed. In the azeotropic distillation, it will be the boiling point at which the solvate and/or water has been driven off.

At this point, the Form I is in the form of a crystal which has precipitated and which may be recovered by isolating the crystal. Typically, this may be accomplished by filtering the crystal or evaporating the solvent or otherwise removing the solvent from the crystal, or the crystal from the solvent. Drying of the solvent, e.g. evaporation at ambient temperature or upon heating, may also be appropriate.

An important feature of Form I over Form II is the ability of Form I not to absorb water readily from the atmosphere. The present invention provides a form of Flavopiridol which has a weight gain due to water of less than 5%, including 4%, 3%, 2%, 1% and less than 1% in fractions (normally about 1–2%) with a Relative Humidity of about 75% and even up to a Relative Humidity of about 90% (weight gain of about 3.5%). Form II, as a solvate/hydrate, showed a slow but continual weight gain of about 4% through about 60% Relative Humidity. Above 60%, Form II showed a weight gain of about 15–20%.

EXAMPLE 1

Preparation of Flavopiridol Form I

Approximately 6 g of Flavopiridol Form II was placed in a 600 mL beaker. 300 mL of Methyl ethyl ketone (MEK) was added slowly, with stirring, to obtain a slurry. The solution was heated slowly to 50° C. until cloudy. The temperature was increased to about 73° C. with stirring and the addition of 100 ml of solvent. As the solution was brought to a strong boil it began to precipitate out and settle to the bottom. The temperature was increased and monitored to 80° C. (boiling point of MEK), for a few minutes to obtain additional precipitate, then removed and allowed to cool to about 55° C. The final volume of 325 mL of solution required filtering through a Buchner funnel, under vacuum, using Whatman #1 filter paper, until dry; resulting in a dense yellow and flocculent chunk-like powder. The structure was confirmed by Mass Spectrometry, Nuclear Magnetic Resonance and Fourier Transform Infra Red, and X-Ray powder diffraction performed on the sample.

EXAMPLE 2

X-Ray Powder Diffraction Methodology

X-ray powder diffraction (XRPD) patterns were obtained on a Scintag XDS 2000 θ/θ diffractometer operating with copper radiation at 45 kV and 40 mA, using a Kevex Psi Peltier-cooled silicon detector. The source slits of 2 and 4 mm, and detector slits of 0.5 and 0.3 mm were used for data collection. Sample obtained was gently milled using an agate mortar and pestle for approximately one minute, placed in a platinum sample holder, and leveled using a glass microscope slide. Powder diffraction patterns of the samples were obtained from 2° to 42° 2θ at 1°/min. Calibration of the XDS 2000 is verified annually using a silicon powder standard.

EXAMPLE 3

Hygroscopicity Screening—Comparison of Form I and Form II

Dynamic Vapor Sorption (DVS) Analysis Studies were Conducted on Form II Versus Form I.
Dynamic Water Vapor Sorption Analysis (DVS)

Form II was studied at 25° C. using a Surface Measurement Systems Dynamic Vapor Sorption DVS-1 analyzer. A sample in the range of about 14.8 mg was placed in a tared quartz sample holder at an initial ambient room humidity setting of about 48% Relative Humidity (RH). A total wet/dry nitrogen flow rate of 200 cc/min was used throughout the study. The following full cycle program was initiated: 30 min at the initial ambient RH, followed by settings of 0, 20, 40, 60, 80, 90, 95 and 98% RH, with exposure time at each humidity set point dependent upon dm/dt being less than 0.001% for 60 min. The maximum time allowed at any one humidity set point was 24 hours. For a full cycle, data collection took about 4 days to complete. After the full cycle the sample was maintained at the same RH as the initial ambient starting RH.

Form I was studied at 25° C. and 40° C. using the DVS-1 analyzer. Data was collected over two full cycles. Samples of 10.4 and 16.7 mg were placed into respective tared quartz sample holders at an initial ambient room humidity setting of about 46% RH and 33% RH, respectively. For this study, an additional 75% RH set point was used. For 2 full cycles, data collection took about 7 days at 25° C. and about 17 days at 40° C. to complete. After completion of each 2 cycle study, the samples were maintained at the same RH as the initial ambient starting RH.

X-ray Powder Diffraction (XRPD) patterns were taken on a Scintag XDS 2000 θ/θ diffractometer operating with copper radiation at 45 kV and 40 mA, using a Kevex Psi Peltier-cooled silicon detector. Source slits of 2 and 4 mm, and detector slits of 0.5 and 0.3 mm were used for data collection. Form II samples were gently milled using an agate mortar and pestle for approximately one minute, placed in a platinum sample pan, and leveled using a glass microscope slide. Samples taken during or post hygroscopicity testing were not milled due to the limited amount of sample available. In each case, powder diffraction patterns were scanned from 2° to 42° 2θ at 1°/minute. Calibration of the XDS 2000 was verified using Silicon powder.

For variable relative humidity experiments, the larger capacity DVS-2 Surface Measurement Systems Dynamic Vapor Sorption analyzer was used. Using a flow rate of 500 cc/min, Form II was held at desired RH settings and sampled periodically for XRPD analysis. Unmilled material was placed in the platinum sample pan and leveled using a glass microscope slide prior to analysis using the above conditions.

Form II showed a slow but continual weight gain through about 60% RH of approximately 4%, and above 60% relative humidity an additional 15–20% weight gain was observed. In contrast, Form I showed an approximate weight gain of 1–2% through about 75% RH, plus an additional estimated 3.5% weight gain through about 90% RH. Above 90% RH, a weight gain of about 30% was observed. Thus, Form II would be considered hygroscopic, while Form I would be considered hygroscopic above 75% RH.

Variable humidity x-ray powder diffraction showed, that, as the humidity is increased there is an apparent decrease in crystallinity in Form II, and a significant change in the XRPD pattern which is presumably due to the loss of ethanol. Whereas Form I apparently retains its crystallinity until extremely high relative humidity is reached, (i.e., >98%) at which point it loses crystallinity and becomes amorphous.

Based upon these results, Form I has superior physical properties relative to Form II for use as a pharmaceutical composition.

EXAMPLE 4

Form II

A reactor is charged under nitrogen atmosphere with (−)-cis-1-methyl-4R-(2,4,6-trimethoxyphenyl)-3S-piperidinol) and acetic anhydride. Boron trifluoride etherate is added at a constant rate while stirring and cooling the resulting solution to 8–20° C. After the addition is complete the resulting mixture is stirred at 20–30° C. for 3–5 hours. The reaction mixture is cooled to 8–12° C. and ice-water is added while stirring followed by addition of aqueous sodium hydroxide until pH 10–11 is attained. The mixture is extracted with ethyl acetate. The ethyl acetate extracts are pooled and concentrated under vacuum. The residue is taken up in methanol and water. Then sodium hydroxide (about 50% aqueous solution) is added. The reaction mixture is stirred at 20–30° C. for 2–3 hours. The mixture is evaporated under reduced pressure at <80° C. The residue is cooled to 15–20° C. and brought to pH 8.5–9.5 using concentrated hydrochloric acid. A solid precipitates, which is collected by filtration washed with demineralized water and dried under reduced pressure to give ((−)-cis-1-methyl-4-(3-acetyl-4,6-dimethoxy-2-hydroxy)phenyl-3-piperidinol).

((−)-cis-1-methyl-4-(3-acetyl-4,6-dimethoxy-2-hydroxy) phenyl-3-piperidinol) is then added portionwise to a stirred suspension of potassium tert. butoxide in dry N,N-dimethylforamide at such a rate that the temperature does not exceed 20° C. After the addition is complete the resulting mixture is stirred for one hour at <30° C. Methyl 2-chlorobenzoate is added at such a rate, that the temperature does not exceed 30° C. the resulting mixture is stirred at 20–30° C. for 4–6 hours. Demineralized water is added, followed by concentrated hydrochloric acid until the pH of the mixture reaches 6–8. The mixture is extracted two times using chloroform. The chloroform extracts are pooled together and concentrated under reduced pressure.

After cooling the remaining oil to ≦40° C., concentrated hydrochloric acid is added. The mixture is then stirred at ≦40° C. for 2 hours or overnight if necessary. After cooling the reaction mixture to 15–30° C., water and chloroform are added. The resulting mixture is basified to pH 8.5–10.5 using sodium hydroxide solution (50%). The phases are separated. The aqueous layer is then extracted with chloroform. The combined organic extracts are evaporated under reduced pressure to yield (−)-cis-2-(2-chlorophenyl)-5,7-dimethoxy-8-[4R-(3S-hydroxy-1-methyl)-piperidinyl]-4H-1-benzopyran-4-one as an oil, which is directly used in the next step without purification.

To (−)-cis-2-(2-chlorophenyl)-5,7-dimethoxy-8-[4R-(3S-hydroxy-1-methyl)-piperidinyl]-4H-1-benzopyran-4-one, quinoline and pyridine hydrochloride are added. The resulting mixture is heated to 160–190° C. while stirring. Stirring is continued while maintaining the temperature at 160–190° C. for 2 hours. After cooling the reaction mixture to 90–110° C. water is added. The resulting mixture is basified to pH 7.5–8.5 using saturated sodium carbonate solution, and extracted twice with a mixture of ethanol and chloroform. The combined extracts are evaporated to dryness to obtain (+)-cis-2-(2-chlorophenyl)-5,7-dihydroxy-8-[4R-(3S-hydroxy-1-methyl)piperidinyl]-4H-1-benzopyran-4-one crude as a brown gum, which is purified as follows.

To (+)-cis-2-(2-chlorophenyl)-5,7-dihydroxy-8-[4R-(3S-hydroxy-1-methyl)piperidinyl]-4H-1-benzopyran-4-one crude, acetone is added. The resulting mixture is stirred at 55–60° C. for 30–60 minutes, then cooled to 15–20° C. and stirred for another 1–2 hours. The precipitated solid is isolated by filtration, washed twice with acetone and dried under reduced pressure to give (+)-cis-2-(2-chlorophenyl)-5,7-dihydroxy-8-[4R-(3S-hydroxy-1-methyl)piperidinyl]-4H-1-benzopyran-4-one in a purified form.

The free base from the previous step is suspended in ethanol and acidified using concentrated hydrochloric acid at such a rate that the temperature does not exceed 30° C. During this process initially all of the solid dissolves and then the hydrochloride precipitates. The suspension is cooled to 0–10° C. and stirred for 1 hour while maintaining the temperature. The crystals are isolated by filtration and washed with cold ethanol to yield (−)-cis-2-(2-chlorophenyl)-5,7-dihydroxy-8-[4R-(3S-hydroxy-1-methyl)piperidinyl]-4H-1-benzopyran-4-one hydrochloride, crude.

To (−)-cis-2-(2-chlorophenyl)-5,7-dihydroxy-8-[4R-(3S-hydroxy-1-methyl)piperidinyl]-4H-1-benzopyran-4-one hydrochloride, crude, ethanol is added. The resulting mixture is heated to 70–79° C., stirred for 1 hour while maintaining the temperature and then filtered while still hot. The filter cake is rinsed with hot ethanol. The filtrate is concentrated by atmospheric distillation, until 60–80% of the volatiles have been removed. The remaining suspension is then cooled to 0–10° C. while isolated by filtration and dried under reduced pressure to give the ethanol solvate of (−)-cis-2-(2-chlorophenyl)-5,7-dihydroxy-8-[4R-(3 S-hydroxy-1-methyl)piperidinyl]-4H-1-benzopyran-4-one hydrochloride, purified as a yellow solid.

After the Form I is recovered, a pharmaceutical composition can be prepared. As used herein, "pharmaceutical composition" means a therapeutically effective amount of Form I with a pharmaceutically acceptable carrier.

A "pharmaceutically acceptable carrier" is an agent which is non-toxic, does not interfere with the therapeutic profile of Form I and is appropriate to the method of administration. Form I is preferably administered by the intravenous route over an appropriate period of time for cancer chemotherapy. Preferably, Form I is mixed with one or more pharmaceutically acceptable carriers. For example, Form I may be mixed with iso-osmotic and pH controlled liquids such as water, dextrose/water or saline/water for injection intravenously into the patient.

An "effective amount" includes a "therapeutically effective amount", "an effective protein kinase inhibiting amount", "an effective cyclin dependent kinase amount" and an effective tumor-inhibiting amount of Form I and will vary with the individual, concomitant therapy, the disease, and other variable factors. An effective amount for Form I will be about the same as for Form II. Typically, the dosage of Form I will be 0.001 mg/kg to 100 mg/kg per day.

Flavopiridol is useful in treating a number of conditions or diseases that benefit from inhibition of protein kinases, and more particularly cyclin dependent kinases as previously described herein. Flavopiridol is expected to be useful in treating a broad range of cancers including, for example, leukemia, mesothelioma and cancers of the lung (large cell, small, cell and non-small cell), colorectal, breast, ovarian, prostate melanoma, renal, uterine body and central nervous system.

All articles and patents cited herein are hereby incorporated herein by reference.

What is claimed is:

1. Anhydrous or solvate-free Form I of (−)-cis-2-(2-chlorophenyl)-5,7-dihydroxy-8-[4R-(3S-hydroxy-1-methyl) piperidinyl]-4H-1-benzopyran-4-one hydrochloride having an X-ray powder diffraction pattern, D space (Å)

12.708

4.323

5.594

5.349

3.590 expressed in terms of "D" spacing.

2. Anhydrous or solvate-free Form I of (−)-cis-2-(2-chlorophenyl)-5,7-dihydroxy-8-[4R-(3S-hydroxy-1-methyl) piperidinyl]-4H-1-benzopyran-4-one hydrochloride having an X-ray powder diffraction pattern,

| D space - Å | Relative Intensity |
| --- | --- |
| 12.708 | Strong |
| 4.323 | Strong |
| 5.594 | Strong |
| 5.349 | Medium |
| 3.590 | Medium |
| 3.366 | Medium |
| 4.209 | Medium |
| 3.395 | Medium |

-continued

| D space - Å | Relative Intensity |
|---|---|
| 3.438 | Medium |
| 4.839 | Medium. | expressed in terms of "D" spacing and relative intensities thereof.

3. Anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride having an X-ray powder diffraction pattern,

| D space - Å | % Relative Intensity |
|---|---|
| 12.708 | 100.0 |
| 4.323 | 75.9 |
| 5.594 | 58.5 |
| 5.349 | 49.5 |
| 3.590 | 46.6 |
| 3.366 | 42.0 |
| 4.209 | 40.7 |
| 3.395 | 39.5 |
| 3.438 | 38.8 |
| 4.839 | 37.1 | expressed in terms of "D" spacing and percentage of relative intensities thereof.

4. Anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride having an X-ray powder diffraction pattern as defined in Table 1,

TABLE 1

| 2 Theta Angle (°) | D Space - Å | Relative Intensity | % Relative Intensity |
|---|---|---|---|
| 6.950 | 12.708 | Strong | 100.0 |
| 20.529 | 4.323 | Strong | 75.9 |
| 15.830 | 5.594 | Strong | 58.5 |
| 16.560 | 5.349 | Medium | 49.5 |
| 24.778 | 3.590 | Medium | 46.6 |
| 26.457 | 3.366 | Medium | 42.0 |
| 21.091 | 4.209 | Medium | 40.7 |
| 26.226 | 3.395 | Medium | 39.5 |
| 25.898 | 3.438 | Medium | 38.8 |
| 18.320 | 4.839 | Medium | 37.1 |
| 8.308 | 10.634 | Medium | 35.7 |
| 23.748 | 3.744 | Medium | 33.4 |
| 13.010 | 6.799 | Medium | 32.4 |
| 30.520 | 2.927 | Medium | 31.0 |
| 27.106 | 3.287 | Weak | 26.2 |
| 31.153 | 2.869 | Weak | 22.4 |
| 29.043 | 3.072 | Weak | 23.7 |
| 14.600 | 6.062 | Weak | 22.4 |
| 19.033 | 4.659 | Weak | 20.6. | expressed in terms of 2 theta angle, "D" spacing, relative intensities and percentage relative intensities thereof.

5. The anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1, wherein said Form I is essentially free of Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate.

6. The anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1, wherein said Form I is essentially free of Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate and other forms of flavopiridol.

7. The anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1, wherein Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate and other forms of flavopiridol are present in less than 4%.

8. A pharmaceutical composition comprising a therapeutically effective amount of anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1 and a pharmaceutically acceptable carrier.

9. A pharmaceutical composition comprising a therapeutically effective amount of anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1, which is essentially free of Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate, and a pharmaceutically acceptable carrier.

10. A pharmaceutical composition comprising a therapeutically effective amount of anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1, which is essentially free of Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate and other forms of flavopiridol, and a pharmaceutically acceptable carrier.

11. A method of treating a patient for cancer comprising administering to said patient a therapeutically effective amount of anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1.

12. The method of claim 11 wherein said anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride is essentially free from Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate or other forms of flavopiridol.

13. A method of inhibiting protein kinases in a patient comprising administering to said patient an effective protein kinase inhibiting amount of anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1.

14. The method of claim 13 wherein said anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride is essentially free from Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate or other forms of flavopiridol.

15. A method of inhibiting cyclin dependent kinases in a patient comprising administering to said patient an effective cyclin dependent kinase inhibiting amount of anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1.

16. The method of claim 15 wherein said anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride is essentially free from Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate or other forms of flavopiridol.

17. A method of making anhydrous or solvate-free Form I of (−)-cis-2-(2-chlorophenyl)-5,7-dihydroxy-8-[4R-(3S-hydroxy-1-methyl)piperidinyl]-4H-1-benzopyran-4-one hydrochloride of claim 1 comprising:

(a) combining a sufficient quantity of Form II of (−)-cis-2-(2-chlorophenyl)-5,7-dihydroxy-8-[4R-(3S-hydroxy-1-methyl)piperidinyl]-4H-1-benzopyran-4-one hydrochloride ethanol solvate with a sufficient amount of an appropriate azeotropic solvent, thus forming an azeotropic mixture;

(b) subjecting said azeotropic mixture to azeotropic distillation sufficient to form Form I of (−)-cis-2-(2-chlorophenyl)-5,7-dihydroxy-8-[4R-(3S-hydroxy-1-methyl)piperidinyl]-4H-1-benzopyran-4-one hydrochloride; and (c) optionally recovering Form I of (−)-cis-2-(2-chlorophenyl)-5,7-dihydroxy-8-[4R-(3S-hydroxy-1-methyl)piperidinyl]-4H-1-benzopyran-4-one hydrochloride therefrom.

18. The method of claim 17 wherein said azeotropic solvent is a ketone solvent.

19. The method of claim 17 wherein said azeotropic solvent is methyl ethyl ketone.

20. The method of claim 17 wherein said Form I of (−)-cis-2-(2-chlorophenyl)-5,7-dihydroxy-8-[4R-(3S-hydroxy-1-methyl)piperidinyl]-4H-1-benzopyran-4-one hydrochloride is recovered by filtration.

21. The method of claim 17 wherein the temperature of said azeotropic distillation is about 73° C. to about 80° C.

22. An anhydrous or solvate-free form of (−)-cis-2-(2-chlorophenyl)-5,7-dihydroxy-8-[4R-(3S-hydroxy-1-methyl)piperidinyl]-4H-1-benzopyran-4-one hydrochloride having less than five percent increase in weight due to water at a relative humidity of about 75%.

* * * * *

UNITED STATES PATENT AND TRADEMARK OFFICE
CERTIFICATE OF CORRECTION

PATENT NO. : 6,576,647 B2
DATED : June 10, 2003
INVENTOR(S) : Gary L. Bafus, Christine M. Harrison-Bowman and Gary Lee Silvey It is certified that error appears in the above-identified patent and that said Letters Patent is hereby corrected as shown below:

Column 7,
Lines 3 and 4, the word "N,N-dimethylforamide" should read -- N,N-dimethylformamide --.
Line 6, the "<30º C" should read -- ≤30ºC --.
Line 8, after "30ºC.", the word "the" should read -- The --.
Line 14, "≦40º C" should read -- ≤40ºC --.
Line 16, reads as "≦40º C. for 2 hours" should read -- ≤40ºC for ≤2 hours --.

Column 8,
Line 22, after "cyclin dependent kinase", insert -- inhibiting --.
Line 34, reads "small, cell and non-small cell)," after the word "small" remove the comma "," to read -- small cell and non-small cell), --.

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,576,647 B2 |
| APPLICATION NO. | : 09/760589 |
| DATED | : June 10, 2003 |
| INVENTOR(S) | : Gary L. Bafus et al. |

Page 1 of 1

It is certified that error appears in the above-identified patent and that said Letters Patent is hereby corrected as shown below:

Column 2, line 10, reads "2Θ." and should read --2θ.--

Column 2, line 12, reads "2Θ." and should read --2θ.--

Column 1, lines 36-38: patent reads "The preferred form is the Flavopiridol hydrochloride ethanol/water solvate form (hereafter "Form II").", and should read --The preferred form is the Flavopiridol hydrochloride ethanol solvate form (hereafter "Form II").--.

Column 3, lines 47-51, reads: ""Form II" means the solvate/hydrate of ethanol/water of (-)cis-2-(2-chlorophenyl)-5,7-dihydroxy-8-[4R-(3S-hydroxy-1-methyl)piperidinyl]-4H-1-benzopyran-4-one hydrochloride as described by x-ray powder diffraction in Table 2, obtained using Cu K-alpha radiation.", and should read --"Form II" means the ethanol solvate of anhydrous (-)cis-2-(2-chlorophenyl)-5,7-dihydroxy-8-[4R-(3S-hydroxy-1-methyl)piperidinyl]-4H-1-benzopyran-4-one hydrochloride as described by X-ray powder diffraction in Table 2, obtained using Cu K-alpha radiation.--.

Column 4, lines 64-65, reads: "Form II, as a solvate/hydrate, showed a slow but continual weight gain of about 4% through about 60% Relative Humidity.", and should read --Form II showed a slow but continual weight gain of about 4% through about 60% Relative Humidity.--.

Signed and Sealed this

Second Day of October, 2007

JON W. DUDAS
*Director of the United States Patent and Trademark Office*